(12) United States Patent
Mannheimer et al.

(10) Patent No.: US 7,689,259 B2
(45) Date of Patent: Mar. 30, 2010

(54) PULSE OXIMETER SENSOR WITH PIECE-WISE FUNCTION

(75) Inventors: Paul D. Mannheimer, Danville, CA (US); Michael E. Fein, Mountain View, CA (US); Marcia Fein, legal representative, Mountain View, CA (US); Charles E. Porges, Orinda, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 585 days.

(21) Appl. No.: 10/798,596

(22) Filed: Mar. 10, 2004

(65) Prior Publication Data

US 2004/0171920 A1    Sep. 2, 2004

Related U.S. Application Data

(63) Continuation of application No. 09/836,050, filed on Apr. 16, 2001, now Pat. No. 6,801,797.

(60) Provisional application No. 60/198,109, filed on Apr. 17, 2000.

(51) Int. Cl.
*A61B 5/1455* (2006.01)

(52) U.S. Cl. ...................... 600/323; 600/331

(58) Field of Classification Search ......... 600/309–310, 600/322–324, 336, 331
See application file for complete search history.

(56) References Cited

U.S. PATENT DOCUMENTS

| | | | |
|---|---|---|---|
| 3,721,813 A | 3/1973 | Condon et al. | |
| 4,086,915 A | 5/1978 | Kofsky et al. | |
| 4,586,513 A | 5/1986 | Hamaguri | |
| 4,603,700 A | 8/1986 | Nichols et al. | |
| 4,621,643 A | 11/1986 | New, Jr. et al. | |
| 4,623,248 A | 11/1986 | Sperinde | |
| 4,653,498 A | 3/1987 | New, Jr. et al. | |
| 4,685,464 A | 8/1987 | Goldberger et al. | |
| 4,694,833 A | 9/1987 | Hamaguri | |
| 4,697,593 A | 10/1987 | Evans et al. | |
| 4,700,708 A | 10/1987 | New, Jr. et al. | |
| 4,714,080 A | 12/1987 | Edgar, Jr. et al. | |
| 4,714,341 A | 12/1987 | Hamaguri et al. | |
| 4,759,369 A | 7/1988 | Taylor | |

(Continued)

FOREIGN PATENT DOCUMENTS

EP    0 571 225 A2    11/1993

(Continued)

OTHER PUBLICATIONS

Such, Hans Olaf; "Optoelectronic Non-invasive Vascular Diagnostics Using multiple Wavelength and Imaging Approach," *Dissertation*, (1998).

*Primary Examiner*—Eric F Winakur

(57) ABSTRACT

A memory in a sensor is used to store multiple coefficients for a physiological parameter. In one embodiment, not only are the sensor's specific calibration coefficients stored in a memory in the sensor for the formula to determine oxygen saturation, but multiple sets of coefficients are stored. The multiple sets apply to different ranges of saturation values to provide a better fit to occur by breaking the R to SpO2 relationship up into different pieces, each described by a different function. The different functions can also be according to different formulas for determining oxygen saturation.

33 Claims, 4 Drawing Sheets

U.S. PATENT DOCUMENTS

| | | | |
|---|---|---|---|
| 4,770,179 A | 9/1988 | New, Jr. et al. | |
| 4,773,422 A | 9/1988 | Isaacson et al. | |
| 4,776,339 A | 10/1988 | Schreiber | |
| 4,781,195 A | 11/1988 | Martin | |
| 4,796,636 A | 1/1989 | Branstetter et al. | |
| 4,800,495 A | 1/1989 | Smith | |
| 4,800,885 A | 1/1989 | Johnson | |
| 4,802,486 A | 2/1989 | Goodman et al. | |
| 4,805,623 A | 2/1989 | Jöbsis | |
| 4,807,630 A | 2/1989 | Malinouskas | |
| 4,807,631 A | 2/1989 | Hersh et al. | |
| 4,819,646 A | 4/1989 | Cheung et al. | |
| 4,819,752 A | 4/1989 | Zelin | |
| 4,824,242 A | 4/1989 | Frick et al. | |
| 4,825,872 A | 5/1989 | Tan et al. | |
| 4,825,879 A | 5/1989 | Tan et al. | |
| 4,830,014 A | 5/1989 | Goodman et al. | |
| 4,832,484 A | 5/1989 | Aoyagi et al. | |
| 4,846,183 A | 7/1989 | Martin | |
| 4,848,901 A | 7/1989 | Hood, Jr. | |
| 4,854,699 A | 8/1989 | Edgar, Jr. | |
| 4,859,056 A | 8/1989 | Prosser et al. | |
| 4,859,057 A | 8/1989 | Taylor et al. | |
| 4,863,265 A | 9/1989 | Flower et al. | |
| 4,865,038 A | 9/1989 | Rich et al. | |
| 4,867,557 A | 9/1989 | Takatani et al. | |
| 4,869,253 A | 9/1989 | Craig, Jr. et al. | |
| 4,869,254 A | 9/1989 | Stone et al. | |
| 4,880,304 A | 11/1989 | Jaeb et al. | |
| 4,883,055 A | 11/1989 | Merrick | |
| 4,883,353 A | 11/1989 | Hansmann et al. | |
| 4,890,619 A | 1/1990 | Hatschek | |
| 4,892,101 A | 1/1990 | Cheung et al. | |
| 4,901,238 A | 2/1990 | Suzuki et al. | |
| 4,908,762 A | 3/1990 | Suzuki et al. | |
| 4,911,167 A | 3/1990 | Corenman et al. | |
| 4,913,150 A | 4/1990 | Cheung et al. | |
| 4,926,867 A | 5/1990 | Kanda et al. | |
| 4,927,264 A | 5/1990 | Shiga et al. | |
| 4,928,692 A | 5/1990 | Goodman et al. | |
| 4,934,372 A | 6/1990 | Corenman et al. | |
| 4,938,218 A | 7/1990 | Goodman et al. | |
| 4,942,877 A | 7/1990 | Sakai et al. | |
| 4,948,248 A | 8/1990 | Lehman | |
| 4,955,379 A | 9/1990 | Hall | |
| 4,960,126 A | 10/1990 | Conlon et al. | |
| 4,964,408 A | 10/1990 | Hink et al. | |
| 4,971,062 A | 11/1990 | Hasebe et al. | |
| 4,974,591 A | 12/1990 | Awazu et al. | |
| 5,007,423 A | 4/1991 | Branstetter et al. | |
| 5,025,791 A | 6/1991 | Niwa | |
| RE033,643 E | 7/1991 | Isaacson et al. | |
| 5,028,787 A | 7/1991 | Rosenthal et al. | |
| 5,040,039 A | 8/1991 | Schmitt et al. | |
| 5,054,488 A | 10/1991 | Muz | |
| 5,055,671 A | 10/1991 | Jones | |
| 5,058,588 A | 10/1991 | Kaestle | |
| 5,065,749 A | 11/1991 | Hasebe et al. | |
| 5,066,859 A | 11/1991 | Karkar et al. | |
| 5,069,213 A | 12/1991 | Polczynski | |
| 5,078,136 A | 1/1992 | Stone et al. | |
| 5,084,327 A | 1/1992 | Stengel | |
| 5,088,493 A | 2/1992 | Giannini et al. | |
| 5,090,410 A | 2/1992 | Saper et al. | |
| 5,094,239 A | 3/1992 | Jaeb et al. | |
| 5,094,240 A | 3/1992 | Muz | |
| 5,099,841 A | 3/1992 | Heinonen et al. | |
| 5,099,842 A | 3/1992 | Mannheimer et al. | |
| H1039 H | 4/1992 | Tripp et al. | |
| 5,104,623 A | 4/1992 | Miller | |
| 5,109,849 A | 5/1992 | Goodman et al. | |
| 5,111,817 A | 5/1992 | Clark et al. | |
| 5,113,861 A | 5/1992 | Rother | |
| 5,125,403 A | 6/1992 | Culp | |
| 5,127,406 A | 7/1992 | Yamaguchi | |
| 5,131,391 A | 7/1992 | Sakai et al. | |
| 5,140,989 A | 8/1992 | Lewis et al. | |
| 5,152,296 A | 10/1992 | Simons | |
| 5,154,175 A | 10/1992 | Gunther | |
| 5,158,082 A | 10/1992 | Jones | |
| 5,170,786 A | 12/1992 | Thomas et al. | |
| 5,188,108 A | 2/1993 | Secker et al. | |
| 5,190,038 A | 3/1993 | Polson et al. | |
| 5,193,542 A | 3/1993 | Missanelli et al. | |
| 5,193,543 A | 3/1993 | Yelderman | |
| 5,203,329 A | 4/1993 | Takatani et al. | |
| 5,209,230 A | 5/1993 | Swedlow et al. | |
| 5,213,099 A | 5/1993 | Tripp et al. | |
| 5,216,598 A | 6/1993 | Branstetter et al. | |
| 5,217,012 A | 6/1993 | Young et al. | |
| 5,217,013 A | 6/1993 | Lewis et al. | |
| 5,218,962 A | 6/1993 | Mannheimer et al. | |
| 5,224,478 A | 7/1993 | Sakai et al. | |
| 5,226,417 A | 7/1993 | Swedlow et al. | |
| 5,228,440 A | 7/1993 | Chung et al. | |
| 5,237,994 A | 8/1993 | Goldberger | |
| 5,239,185 A | 8/1993 | Ito et al. | |
| 5,246,002 A | 9/1993 | Prosser | |
| 5,246,003 A | 9/1993 | DeLonzor | |
| 5,247,931 A | 9/1993 | Norwood | |
| 5,247,932 A | 9/1993 | Chung et al. | |
| 5,249,576 A | 10/1993 | Goldberger et al. | |
| 5,253,645 A | 10/1993 | Friedman et al. | |
| 5,253,646 A | 10/1993 | Delpy et al. | |
| 5,259,381 A | 11/1993 | Cheung et al. | |
| 5,259,761 A | 11/1993 | Schnettler et al. | |
| 5,263,244 A | 11/1993 | Centa et al. | |
| 5,267,562 A | 12/1993 | Ukawa et al. | |
| 5,267,563 A | 12/1993 | Swedlow et al. | |
| 5,273,036 A | 12/1993 | Kronberg et al. | |
| 5,275,159 A | 1/1994 | Griebel | |
| 5,279,295 A | 1/1994 | Martens et al. | |
| 5,285,783 A | 2/1994 | Secker | |
| 5,285,784 A | 2/1994 | Seeker | |
| 5,287,853 A | 2/1994 | Vester et al. | |
| 5,291,884 A | 3/1994 | Heinemann et al. | |
| 5,297,548 A | 3/1994 | Pologe | |
| 5,299,120 A | 3/1994 | Kaestle | |
| 5,299,570 A | 4/1994 | Hatschek | |
| 5,309,908 A | 5/1994 | Friedman et al. | |
| 5,311,865 A | 5/1994 | Mayeux | |
| 5,313,940 A | 5/1994 | Fuse et al. | |
| 5,323,776 A | 6/1994 | Blakeley et al. | |
| 5,329,922 A | 7/1994 | Atlee, III | |
| 5,337,744 A | 8/1994 | Branigan | |
| 5,339,810 A | 8/1994 | Ivers et al. | |
| 5,343,818 A | 9/1994 | McCarthy et al. | |
| 5,343,869 A | 9/1994 | Pross et al. | |
| 5,348,003 A | 9/1994 | Caro | |
| 5,348,004 A | 9/1994 | Hollub et al. | |
| 5,348,005 A | 9/1994 | Merrick et al. | |
| 5,349,519 A | 9/1994 | Kaestle | |
| 5,349,952 A | 9/1994 | McCarthy et al. | |
| 5,349,953 A | 9/1994 | McCarthy et al. | |
| 5,351,685 A | 10/1994 | Potratz | |
| 5,353,799 A | 10/1994 | Chance | |
| 5,355,880 A | 10/1994 | Thomas et al. | |
| 5,355,882 A | 10/1994 | Ukawa et al. | |
| 5,361,758 A | 11/1994 | Hall et al. | |
| 5,365,066 A | 11/1994 | Krueger, Jr. et al. | |
| 5,368,025 A | 11/1994 | Young et al. | |
| 5,368,026 A | 11/1994 | Swedlow et al. | |
| 5,368,224 A | 11/1994 | Richardson et al. | |
| 5,372,136 A | 12/1994 | Steuer et al. | |

| Patent | Type | Date | Inventor |
|---|---|---|---|
| 5,377,675 | A | 1/1995 | Ruskewicz et al. |
| 5,385,143 | A | 1/1995 | Aoyagi |
| 5,386,827 | A | 2/1995 | Chance et al. |
| 5,387,122 | A | 2/1995 | Goldberger et al. |
| 5,390,670 | A | 2/1995 | Centa et al. |
| 5,392,777 | A | 2/1995 | Swedlow et al. |
| 5,398,680 | A | 3/1995 | Polson et al. |
| 5,402,777 | A | 4/1995 | Warring et al. |
| 5,411,023 | A | 5/1995 | Morris, Sr. et al. |
| 5,411,024 | A | 5/1995 | Thomas et al. |
| 5,413,099 | A | 5/1995 | Schmidt et al. |
| 5,413,100 | A | 5/1995 | Barthelemy et al. |
| 5,413,101 | A | 5/1995 | Sugiura |
| 5,413,102 | A | 5/1995 | Schmidt et al. |
| 5,417,207 | A | 5/1995 | Young et al. |
| 5,421,329 | A | 6/1995 | Casciani et al. |
| 5,425,360 | A | 6/1995 | Nelson |
| 5,425,362 | A | 6/1995 | Siker et al. |
| 5,427,093 | A | 6/1995 | Ogawa et al. |
| 5,429,128 | A | 7/1995 | Cadell et al. |
| 5,429,129 | A | 7/1995 | Lovejoy et al. |
| 5,431,159 | A | 7/1995 | Baker et al. |
| 5,431,170 | A | 7/1995 | Mathews |
| 5,437,275 | A | 8/1995 | Amundsen et al. |
| 5,438,986 | A | 8/1995 | Disch et al. |
| 5,448,991 | A | 9/1995 | Polson et al. |
| 5,452,717 | A | 9/1995 | Branigan et al. |
| 5,465,714 | A | 11/1995 | Scheuing |
| 5,469,845 | A | 11/1995 | DeLonzor et al. |
| RE035,122 | E | 12/1995 | Corenman et al. |
| 5,482,034 | A | 1/1996 | Lewis et al. |
| 5,482,036 | A | 1/1996 | Diab et al. |
| 5,483,646 | A | 1/1996 | Uchikoga |
| 5,485,847 | A | 1/1996 | Baker, Jr. |
| 5,490,505 | A | 2/1996 | Diab et al. |
| 5,490,523 | A | 2/1996 | Isaacson et al. |
| 5,491,299 | A | 2/1996 | Naylor et al. |
| 5,494,032 | A | 2/1996 | Robinson et al. |
| 5,497,771 | A | 3/1996 | Rosenheimer |
| 5,499,627 | A | 3/1996 | Steuer et al. |
| 5,503,148 | A | 4/1996 | Pologe et al. |
| 5,505,199 | A | 4/1996 | Kim |
| 5,507,286 | A | 4/1996 | Solenberger |
| 5,517,988 | A | 5/1996 | Gerhard |
| 5,520,177 | A | 5/1996 | Ogawa et al. |
| 5,521,851 | A | 5/1996 | Wei et al. |
| 5,522,388 | A | 6/1996 | Ishikawa et al. |
| 5,524,617 | A | 6/1996 | Mannheimer |
| 5,529,064 | A | 6/1996 | Rall et al. |
| 5,533,507 | A | 7/1996 | Potratz et al. |
| 5,551,423 | A | 9/1996 | Sugiura |
| 5,551,424 | A | 9/1996 | Morrison et al. |
| 5,553,614 | A | 9/1996 | Chance |
| 5,553,615 | A | 9/1996 | Carim et al. |
| 5,555,882 | A | 9/1996 | Richardson et al. |
| 5,558,096 | A | 9/1996 | Palatnik |
| 5,560,355 | A | 10/1996 | Merchant et al. |
| 5,564,417 | A | 10/1996 | Chance |
| 5,575,284 | A | 11/1996 | Athan et al. |
| 5,575,285 | A | 11/1996 | Takanashi et al. |
| 5,577,500 | A | 11/1996 | Potratz |
| 5,582,169 | A | 12/1996 | Oda et al. |
| 5,584,296 | A | 12/1996 | Cui et al. |
| 5,588,425 | A | 12/1996 | Sackner et al. |
| 5,588,427 | A | 12/1996 | Tien |
| 5,590,652 | A | 1/1997 | Inai |
| 5,595,176 | A | 1/1997 | Yamaura |
| 5,596,986 | A | 1/1997 | Goldfarb |
| 5,611,337 | A | 3/1997 | Bukta |
| 5,617,852 | A | 4/1997 | MacGregor |
| 5,619,992 | A | 4/1997 | Guthrie et al. |
| 5,626,140 | A | 5/1997 | Feldman et al. |
| 5,630,413 | A | 5/1997 | Thomas et al. |
| 5,632,272 | A | 5/1997 | Diab et al. |
| 5,632,273 | A | 5/1997 | Suzuki |
| 5,634,459 | A | 6/1997 | Gardosi |
| 5,638,593 | A | 6/1997 | Gerhardt et al. |
| 5,638,818 | A | 6/1997 | Diab et al. |
| 5,645,060 | A | 7/1997 | Yorkey et al. |
| 5,645,440 | A | 7/1997 | Tobler et al. |
| 5,660,567 | A | 8/1997 | Nierlich et al. |
| 5,662,105 | A | 9/1997 | Tien |
| 5,662,106 | A | 9/1997 | Swedlow et al. |
| 5,666,952 | A | 9/1997 | Fuse et al. |
| 5,671,529 | A | 9/1997 | Nelson |
| 5,673,692 | A | 10/1997 | Schulze et al. |
| 5,673,693 | A | 10/1997 | Solenberger |
| 5,676,139 | A | 10/1997 | Goldberger et al. |
| 5,676,141 | A | 10/1997 | Hollub |
| 5,678,544 | A | 10/1997 | DeLonzor et al. |
| 5,680,857 | A | 10/1997 | Pelikan et al. |
| 5,685,299 | A | 11/1997 | Diab et al. |
| 5,685,301 | A | 11/1997 | Klomhaus |
| 5,687,719 | A | 11/1997 | Sato et al. |
| 5,687,722 | A | 11/1997 | Tien et al. |
| 5,692,503 | A | 12/1997 | Kuenstner |
| 5,692,505 | A | 12/1997 | Fouts |
| 5,709,205 | A | 1/1998 | Bukta |
| 5,713,355 | A | 2/1998 | Richardson et al. |
| 5,724,967 | A | 3/1998 | Venkatachalam |
| 5,727,547 | A | 3/1998 | Levinson et al. |
| 5,731,582 | A | 3/1998 | West |
| D393,830 | S | 4/1998 | Tobler et al. |
| 5,743,260 | A | 4/1998 | Chung et al. |
| 5,743,263 | A | 4/1998 | Baker, Jr. |
| 5,746,206 | A | 5/1998 | Mannheimer |
| 5,746,697 | A | 5/1998 | Swedlow et al. |
| 5,752,914 | A | 5/1998 | Delonzor et al. |
| 5,755,226 | A | 5/1998 | Carim et al. |
| 5,758,644 | A | 6/1998 | Diab et al. |
| 5,760,910 | A | 6/1998 | Lepper, Jr. et al. |
| 5,766,125 | A | 6/1998 | Aoyagi et al. |
| 5,766,127 | A | 6/1998 | Pologe et al. |
| 5,769,785 | A | 6/1998 | Diab et al. |
| 5,772,587 | A | 6/1998 | Gratton et al. |
| 5,774,213 | A | 6/1998 | Trebino et al. |
| 5,776,058 | A | 7/1998 | Levinson et al. |
| 5,776,059 | A | 7/1998 | Kaestle |
| 5,779,630 | A | 7/1998 | Fein et al. |
| 5,779,631 | A | 7/1998 | Chance |
| 5,782,237 | A | 7/1998 | Casciani et al. |
| 5,782,756 | A | 7/1998 | Mannheimer |
| 5,782,757 | A | 7/1998 | Diab et al. |
| 5,782,758 | A | 7/1998 | Ausec et al. |
| 5,783,821 | A | 7/1998 | Costello, Jr. |
| 5,786,592 | A | 7/1998 | Hök |
| 5,790,729 | A | 8/1998 | Pologe et al. |
| 5,792,052 | A | 8/1998 | Isaacson et al. |
| 5,795,292 | A | 8/1998 | Lewis et al. |
| 5,797,841 | A | 8/1998 | DeLonzor et al. |
| 5,800,348 | A | 9/1998 | Kaestle |
| 5,800,349 | A | 9/1998 | Isaacson et al. |
| 5,803,910 | A | 9/1998 | Potratz |
| 5,807,246 | A | 9/1998 | Sakaguchi et al. |
| 5,807,247 | A | 9/1998 | Merchant et al. |
| 5,807,248 | A | 9/1998 | Mills |
| 5,810,723 | A | 9/1998 | Aldrich |
| 5,810,724 | A | 9/1998 | Gronvall |
| 5,813,980 | A | 9/1998 | Levinson et al. |
| 5,817,008 | A | 10/1998 | Rafert et al. |
| 5,817,009 | A | 10/1998 | Rosenheimer et al. |
| 5,817,010 | A | 10/1998 | Hibl |
| 5,818,985 | A | 10/1998 | Merchant et al. |
| 5,820,550 | A | 10/1998 | Polson et al. |
| 5,823,950 | A | 10/1998 | Diab et al. |
| 5,823,952 | A | 10/1998 | Levinson et al. |

| | | | | | | |
|---|---|---|---|---|---|---|
| 5,827,182 | A | 10/1998 | Raley et al. | 6,035,223 A | 3/2000 | Baker, Jr. |
| 5,830,135 | A | 11/1998 | Bosque et al. | 6,036,642 A | 3/2000 | Diab et al. |
| 5,830,136 | A | 11/1998 | DeLonzor et al. | 6,041,247 A | 3/2000 | Weckstrom et al. |
| 5,830,137 | A | 11/1998 | Scharf | 6,044,283 A | 3/2000 | Fein et al. |
| 5,839,439 | A | 11/1998 | Nierlich et al. | 6,047,201 A | 4/2000 | Jackson, III |
| RE36,000 | E | 12/1998 | Swedlow et al. | 6,061,584 A | 5/2000 | Lovejoy et al. |
| 5,842,979 | A | 12/1998 | Jarman et al. | 6,064,898 A | 5/2000 | Aldrich |
| 5,842,981 | A | 12/1998 | Larsen et al. | 6,064,899 A | 5/2000 | Fein et al. |
| 5,842,982 | A | 12/1998 | Mannheimer | 6,067,462 A | 5/2000 | Diab et al. |
| 5,846,190 | A | 12/1998 | Woehrle | 6,073,038 A | 6/2000 | Wang et al. |
| 5,851,178 | A | 12/1998 | Aronow | 6,078,833 A | 6/2000 | Hueber |
| 5,851,179 | A | 12/1998 | Ritson et al. | 6,081,735 A | 6/2000 | Diab et al. |
| 5,853,364 | A | 12/1998 | Baker, Jr. et al. | 6,081,742 A | 6/2000 | Amano et al. |
| 5,860,919 | A | 1/1999 | Kiani-Azarbayjany et al. | 6,083,157 A | 7/2000 | Noller |
| 5,865,736 | A | 2/1999 | Baker, Jr. et al. | 6,083,172 A | 7/2000 | Baker, Jr. et al. |
| 5,871,442 | A | 2/1999 | Madarasz et al. | 6,088,607 A | 7/2000 | Diab et al. |
| 5,879,294 | A | 3/1999 | Anderson et al. | 6,094,592 A | 7/2000 | Yorkey et al. |
| 5,885,213 | A | 3/1999 | Richardson et al. | 6,095,974 A | 8/2000 | Shemwell et al. |
| 5,890,929 | A | 4/1999 | Mills et al. | 6,104,938 A | 8/2000 | Huiku et al. |
| 5,891,021 | A | 4/1999 | Dillon et al. | 6,112,107 A | 8/2000 | Hannula |
| 5,891,022 | A | 4/1999 | Pologe | 6,113,541 A | 9/2000 | Dias et al. |
| 5,891,024 | A | 4/1999 | Jarman et al. | 6,115,621 A | 9/2000 | Chin |
| 5,891,025 | A | 4/1999 | Buschmann et al. | 6,122,535 A | 9/2000 | Kaestle et al. |
| 5,891,026 | A | 4/1999 | Wang et al. | 6,133,994 A | 10/2000 | Mathews et al. |
| 5,902,235 | A | 5/1999 | Lewis et al. | 6,135,952 A | 10/2000 | Coetzee |
| 5,910,108 | A | 6/1999 | Solenberger | 6,144,444 A | 11/2000 | Haworth et al. |
| 5,911,690 | A | 6/1999 | Rall | 6,144,867 A | 11/2000 | Walker et al. |
| 5,912,656 | A | 6/1999 | Tham et al. | 6,144,868 A | 11/2000 | Parker |
| 5,913,819 | A | 6/1999 | Taylor et al. | 6,149,481 A | 11/2000 | Wang et al. |
| 5,916,154 | A | 6/1999 | Hobbs et al. | 6,150,951 A | 11/2000 | Olejniczak |
| 5,916,155 | A | 6/1999 | Levinson et al. | 6,151,107 A | 11/2000 | Schöllermann et al. |
| 5,919,133 | A | 7/1999 | Taylor et al. | 6,151,518 A | 11/2000 | Hayashi |
| 5,919,134 | A | 7/1999 | Diab | 6,152,754 A | 11/2000 | Gerhardt et al. |
| 5,920,263 | A | 7/1999 | Huttenhoff et al. | 6,154,667 A | 11/2000 | Miura et al. |
| 5,921,921 | A | 7/1999 | Potratz et al. | 6,157,850 A | 12/2000 | Diab et al. |
| 5,922,607 | A | 7/1999 | Bernreuter | 6,163,175 A | 12/2000 | Larsen et al. |
| 5,924,979 | A | 7/1999 | Swedlow et al. | 6,163,715 A | 12/2000 | Larsen et al. |
| 5,924,980 | A | 7/1999 | Coetzee | 6,165,005 A | 12/2000 | Mills et al. |
| 5,924,982 | A | 7/1999 | Chin | 6,173,196 B1 | 1/2001 | Delonzor et al. |
| 5,924,985 | A | 7/1999 | Jones | 6,178,343 B1 | 1/2001 | Bindszus et al. |
| 5,934,277 | A | 8/1999 | Mortz | 6,181,958 B1 | 1/2001 | Steuer et al. |
| 5,934,925 | A | 8/1999 | Tobler et al. | 6,181,959 B1 | 1/2001 | Schöllermann et al. |
| 5,940,182 | A | 8/1999 | Lepper, Jr. et al. | 6,184,521 B1 | 2/2001 | Coffin, IV et al. |
| 5,954,644 | A | 9/1999 | Dettling et al. | 6,188,470 B1 | 2/2001 | Grace |
| 5,960,610 | A | 10/1999 | Levinson et al. | 6,192,260 B1 | 2/2001 | Chance |
| 5,961,450 | A | 10/1999 | Merchant et al. | 6,195,575 B1 | 2/2001 | Levinson |
| 5,961,452 | A | 10/1999 | Chung et al. | 6,198,951 B1 | 3/2001 | Kosuda et al. |
| 5,964,701 | A | 10/1999 | Asada et al. | 6,206,830 B1 | 3/2001 | Diab et al. |
| 5,971,930 | A | 10/1999 | Elghazzawi | 6,213,952 B1 | 4/2001 | Finarov et al. |
| 5,978,691 | A | 11/1999 | Mills | 6,217,523 B1 | 4/2001 | Amano et al. |
| 5,978,693 | A | 11/1999 | Hamilton et al. | 6,222,189 B1 | 4/2001 | Misner et al. |
| 5,983,122 | A | 11/1999 | Jarman et al. | 6,226,539 B1 | 5/2001 | Potratz |
| 5,987,343 | A | 11/1999 | Kinast | 6,226,540 B1 | 5/2001 | Bernreuter |
| 5,991,648 | A | 11/1999 | Levin | 6,229,856 B1 | 5/2001 | Diab et al. |
| 5,995,855 | A | 11/1999 | Kiani et al. | 6,230,035 B1 | 5/2001 | Aoyagi et al. |
| 5,995,856 | A | 11/1999 | Mannheimer et al. | 6,233,470 B1 | 5/2001 | Tsuchiya |
| 5,995,858 | A | 11/1999 | Kinast | 6,236,871 B1 | 5/2001 | Tsuchiya |
| 5,995,859 | A | 11/1999 | Takahashi | 6,236,872 B1 | 5/2001 | Diab et al. |
| 5,997,343 | A | 12/1999 | Mills et al. | 6,240,305 B1 | 5/2001 | Tsuchiya |
| 5,999,834 | A | 12/1999 | Wang et al. | 6,253,097 B1 | 6/2001 | Aronow et al. |
| 6,002,952 | A | 12/1999 | Diab et al. | 6,253,098 B1 | 6/2001 | Walker et al. |
| 6,005,658 | A | 12/1999 | Kaluza et al. | 6,256,523 B1 | 7/2001 | Diab et al. |
| 6,006,120 | A | 12/1999 | Levin | 6,256,524 B1 | 7/2001 | Walker et al. |
| 6,011,985 | A | 1/2000 | Athan et al. | 6,261,236 B1 | 7/2001 | Grimblatov |
| 6,011,986 | A | 1/2000 | Diab et al. | 6,263,221 B1 | 7/2001 | Chance et al. |
| 6,014,576 | A | 1/2000 | Raley et al. | 6,263,222 B1 | 7/2001 | Diab et al. |
| 6,018,673 | A | 1/2000 | Chin et al. | 6,263,223 B1 | 7/2001 | Shepherd et al. |
| 6,018,674 | A | 1/2000 | Aronow | 6,266,546 B1 | 7/2001 | Steuer et al. |
| 6,022,321 | A | 2/2000 | Amano et al. | 6,266,547 B1 | 7/2001 | Walker et al. |
| 6,023,541 | A | 2/2000 | Merchant et al. | 6,272,363 B1 | 8/2001 | Casciani et al. |
| 6,026,312 | A | 2/2000 | Shemwell et al. | 6,278,522 B1 | 8/2001 | Lepper, Jr. et al. |
| 6,026,314 | A | 2/2000 | Amerov et al. | 6,280,213 B1 | 8/2001 | Tobler et al. |
| 6,031,603 | A | 2/2000 | Fine et al. | 6,280,381 B1 | 8/2001 | Malin et al. |

| | | |
|---|---|---|
| 6,285,894 B1 | 9/2001 | Oppelt et al. |
| 6,285,895 B1 | 9/2001 | Ristolainen et al. |
| 6,285,896 B1 | 9/2001 | Tobler et al. |
| 6,298,252 B1 | 10/2001 | Kovach et al. |
| 6,308,089 B1 | 10/2001 | Von der Ruhr et al. |
| 6,321,100 B1 | 11/2001 | Parker |
| 6,330,468 B1 | 12/2001 | Scharf |
| 6,334,065 B1 | 12/2001 | Al-Ali et al. |
| 6,339,715 B1 | 1/2002 | Bahr et al. |
| 6,343,223 B1 | 1/2002 | Chin et al. |
| 6,343,224 B1 | 1/2002 | Parker |
| 6,349,228 B1 | 2/2002 | Kiani et al. |
| 6,351,658 B1 | 2/2002 | Middleman et al. |
| 6,353,750 B1 | 3/2002 | Kimura et al. |
| 6,356,774 B1 | 3/2002 | Bernstein et al. |
| 6,360,113 B1 | 3/2002 | Dettling |
| 6,360,114 B1 | 3/2002 | Diab et al. |
| 6,361,501 B1 | 3/2002 | Amano et al. |
| 6,363,269 B1 | 3/2002 | Hanna et al. |
| 6,370,408 B1 | 4/2002 | Merchant et al. |
| 6,370,409 B1 | 4/2002 | Chung et al. |
| 6,374,129 B1 | 4/2002 | Chin et al. |
| 6,377,829 B1 | 4/2002 | Al-Ali et al. |
| 6,381,479 B1 | 4/2002 | Norris |
| 6,381,480 B1 | 4/2002 | Stoddar et al. |
| 6,385,471 B1 | 5/2002 | Mortz |
| 6,385,821 B1 | 5/2002 | Modgil et al. |
| 6,388,240 B2 | 5/2002 | Schulz et al. |
| 6,393,310 B1 | 5/2002 | Kuenstner |
| 6,397,091 B2 | 5/2002 | Diab et al. |
| 6,397,092 B1 | 5/2002 | Norris et al. |
| 6,397,093 B1 | 5/2002 | Aldrich |
| 6,400,971 B1 | 6/2002 | Finarov et al. |
| 6,400,972 B1 | 6/2002 | Fine |
| 6,402,690 B1 | 6/2002 | Rhee et al. |
| 6,408,198 B1 | 6/2002 | Hanna et al. |
| 6,411,832 B1 | 6/2002 | Guthermann |
| 6,411,833 B1 | 6/2002 | Baker, Jr. et al. |
| 6,419,671 B1 | 7/2002 | Lemberg |
| 6,421,549 B1 | 7/2002 | Jacques |
| 6,430,423 B2 | 8/2002 | DeLonzor et al. |
| 6,430,513 B1 | 8/2002 | Wang et al. |
| 6,438,399 B1 | 8/2002 | Kurth |
| 6,453,183 B1 | 9/2002 | Walker |
| 6,463,310 B1 | 10/2002 | Swedlow et al. |
| 6,463,311 B1 | 10/2002 | Diab |
| 6,466,808 B1 | 10/2002 | Chin et al. |
| 6,470,200 B2 | 10/2002 | Walker et al. |
| 6,496,711 B1 | 12/2002 | Athan et al. |
| 6,498,942 B1 | 12/2002 | Esenaliev et al. |
| 6,501,975 B2 | 12/2002 | Diab et al. |
| 6,512,937 B2 | 1/2003 | Blank et al. |
| 6,515,273 B2 | 2/2003 | Al-Ali |
| 6,519,486 B1 | 2/2003 | Edgar, Jr. et al. |
| 6,519,487 B1 | 2/2003 | Parker |
| 6,525,386 B1 | 2/2003 | Mills et al. |
| 6,526,300 B1 | 2/2003 | Kiani et al. |
| 6,526,301 B2 | 2/2003 | Larsen et al. |
| 6,541,756 B2 | 4/2003 | Schulz et al. |
| 6,542,764 B1 | 4/2003 | Al-Ali et al. |
| 6,549,284 B1 | 4/2003 | Boas et al. |
| 6,553,242 B1 | 4/2003 | Sarussi |
| 6,553,243 B2 | 4/2003 | Gurley |
| 6,564,088 B1 | 5/2003 | Soller et al. |
| 6,574,491 B2 | 6/2003 | Elghazzawi |
| 6,580,086 B1 | 6/2003 | Schulz et al. |
| 6,584,336 B1 | 6/2003 | Ali et al. |
| 6,587,704 B1 | 7/2003 | Fine et al. |
| 6,594,511 B2 | 7/2003 | Stone et al. |
| 6,594,513 B1 | 7/2003 | Jobsis et al. |
| 6,597,933 B2 | 7/2003 | Kiani et al. |
| 6,606,511 B1 | 8/2003 | Ali et al. |
| 6,615,064 B1 | 9/2003 | Aldrich |
| 6,615,065 B1 | 9/2003 | Barrett et al. |
| 6,622,034 B1 | 9/2003 | Gorski et al. |
| 6,643,530 B2 | 11/2003 | Diab et al. |
| 6,647,280 B2 | 11/2003 | Bahr et al. |
| 6,650,917 B2 | 11/2003 | Diab et al. |
| 6,654,622 B1 | 11/2003 | Eberhard et al. |
| 6,654,624 B2 | 11/2003 | Diab et al. |
| 6,658,276 B2 | 12/2003 | Kianl et al. |
| 6,662,033 B2 | 12/2003 | Casciani et al. |
| 6,671,526 B1 | 12/2003 | Aoyagi et al. |
| 6,671,528 B2 | 12/2003 | Steuer et al. |
| 6,671,530 B2 | 12/2003 | Chung et al. |
| 6,671,531 B2 | 12/2003 | Al-Ali et al. |
| 6,675,031 B1 | 1/2004 | Porges et al. |
| 6,678,543 B2 | 1/2004 | Diab et al. |
| 6,681,126 B2 | 1/2004 | Solenberger |
| 6,681,128 B2 | 1/2004 | Steuer et al. |
| 6,681,454 B2 | 1/2004 | Modgil et al. |
| 6,684,090 B2 | 1/2004 | Ali et al. |
| 6,684,091 B2 | 1/2004 | Parker |
| 6,694,160 B2 | 2/2004 | Chin |
| RE38,476 E | 3/2004 | Diab et al. |
| 6,699,194 B1 | 3/2004 | Diab et al. |
| 6,708,049 B1 | 3/2004 | Berson et al. |
| 6,714,803 B1 | 3/2004 | Mortz |
| 6,714,804 B2 | 3/2004 | Al-Ali et al. |
| RE38,492 E | 4/2004 | Diab et al. |
| 6,721,584 B2 | 4/2004 | Baker, Jr. et al. |
| 6,721,585 B1 | 4/2004 | Parker |
| 6,725,075 B2 | 4/2004 | Al-Ali |
| 6,735,459 B2 | 5/2004 | Parker |
| 6,745,060 B2 | 6/2004 | Diab et al. |
| 6,748,253 B2 | 6/2004 | Norris et al. |
| 6,760,609 B2 | 7/2004 | Jacques |
| 6,763,255 B2 | 7/2004 | DeLonzor et al. |
| 6,770,028 B1 | 8/2004 | Ali et al. |
| 6,771,994 B2 | 8/2004 | Kiani et al. |
| 6,792,300 B1 | 9/2004 | Diab et al. |
| 6,793,654 B2 | 9/2004 | Lemberg |
| 6,801,797 B2 * | 10/2004 | Mannheimer et al. ....... 600/323 |
| 6,810,277 B2 | 10/2004 | Edgar, Jr. et al. |
| 6,813,511 B2 | 11/2004 | Diab et al. |
| 6,816,741 B2 | 11/2004 | Diab |
| 6,826,419 B2 | 11/2004 | Diab et al. |
| 6,830,711 B2 | 12/2004 | Mills et al. |
| 6,836,679 B2 | 12/2004 | Baker, Jr. et al. |
| 6,845,256 B2 | 1/2005 | Chin et al. |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,916,289 B2 | 7/2005 | Schnall |
| 6,939,307 B1 | 9/2005 | Dunlop |
| 6,950,687 B2 | 9/2005 | Al-Ali |
| 6,971,580 B2 | 12/2005 | DeLonzor et al. |
| 6,979,812 B2 | 12/2005 | Al-Ali |
| 6,993,371 B2 | 1/2006 | Kiani et al. |
| 6,996,427 B2 | 2/2006 | Ali et al. |
| 7,003,339 B2 | 2/2006 | Diab et al. |
| 7,006,855 B1 | 2/2006 | Sarussi |
| 7,024,233 B2 | 4/2006 | Ali et al. |
| 7,035,697 B1 | 4/2006 | Brown |
| 7,039,449 B2 | 5/2006 | Al-Ali |
| 7,043,289 B2 | 5/2006 | Fine et al. |
| 7,047,055 B2 | 5/2006 | Boaz et al. |
| 7,048,687 B1 | 5/2006 | Reuss et al. |
| 7,062,307 B2 | 6/2006 | Norris et al. |
| 7,067,893 B2 | 6/2006 | Mills et al. |
| 7,072,702 B2 | 7/2006 | Edgar, Jr. et al. |
| RE039,268 E | 9/2006 | Merrick et al. |
| 7,130,671 B2 | 10/2006 | Baker, Jr. et al. |
| 7,132,641 B2 | 11/2006 | Schulz et al. |
| 7,198,778 B2 | 4/2007 | Mannheimer et al. |
| 7,215,984 B2 | 5/2007 | Diab et al. |

| | | |
|---|---|---|
| 7,254,433 B2 | 8/2007 | Diab et al. |
| 7,272,425 B2 | 9/2007 | Al-Ali |
| 7,315,753 B2 | 1/2008 | Baker, Jr. et al. |
| 7,428,432 B2 | 9/2008 | Ali et al. |
| 7,457,652 B2 | 11/2008 | Porges et al. |
| 2001/0021803 A1 | 9/2001 | Blank et al. |
| 2002/0026109 A1 | 2/2002 | Diab et al. |
| 2002/0028990 A1 | 3/2002 | Shepherd et al. |
| 2002/0103423 A1 | 8/2002 | Chin et al. |
| 2002/0128544 A1 | 9/2002 | Diab et al. |
| 2003/0018243 A1 | 1/2003 | Gerhardt et al. |
| 2003/0045785 A1 | 3/2003 | Diab et al. |
| 2003/0132495 A1 | 7/2003 | Mills et al. |
| 2003/0135099 A1 | 7/2003 | Al-Ali et al. |
| 2003/0162414 A1 | 8/2003 | Schulz et al. |
| 2003/0197679 A1 | 10/2003 | Ali et al. |
| 2004/0059209 A1 | 3/2004 | Al-Ali et al. |
| 2004/0064020 A1 | 4/2004 | Diab et al. |
| 2004/0068164 A1 | 4/2004 | Diab et al. |
| 2004/0097797 A1 | 5/2004 | Porges et al. |
| 2004/0116789 A1 | 6/2004 | Boas et al. |
| 2004/0133087 A1 | 7/2004 | Ali et al. |
| 2004/0133088 A1 | 7/2004 | Al-Ali et al. |
| 2004/0147823 A1 | 7/2004 | Kiani et al. |
| 2004/0147824 A1 | 7/2004 | Diab et al. |
| 2004/0152965 A1 | 8/2004 | Diab et al. |
| 2004/0158134 A1 | 8/2004 | Diab et al. |
| 2004/0158135 A1 | 8/2004 | Baker, Jr. et al. |
| 2004/0162472 A1 | 8/2004 | Berson et al. |
| 2004/0176671 A1 | 9/2004 | Fine et al. |
| 2004/0181134 A1 | 9/2004 | Baker, Jr. et al. |
| 2004/0204636 A1 | 10/2004 | Diab et al. |
| 2004/0204637 A1 | 10/2004 | Diab et al. |
| 2004/0204638 A1 | 10/2004 | Diab et al. |
| 2004/0204639 A1 | 10/2004 | Casciani et al. |
| 2004/0210146 A1 | 10/2004 | Diab et al. |
| 2004/0236196 A1 | 11/2004 | Diab et al. |
| 2005/0020894 A1 | 1/2005 | Norris et al. |
| 2005/0033128 A1 | 2/2005 | Ali et al. |
| 2005/0033129 A1 | 2/2005 | Edgar Jr. et al. |
| 2005/0043600 A1 | 2/2005 | Diab et al. |
| 2005/0065417 A1 | 3/2005 | Ali et al. |
| 2005/0283059 A1 | 12/2005 | Iyer et al. |
| 2006/0030764 A1 | 2/2006 | Porges et al. |
| 2006/0161054 A1 | 7/2006 | Reuss et al. |
| 2006/0200018 A1 | 9/2006 | Al-Ali |
| 2006/0224059 A1 | 10/2006 | Swedlow et al. |
| 2006/0258926 A1 | 11/2006 | Ali et al. |
| 2007/0112260 A1 | 5/2007 | Diab et al. |
| 2008/0039701 A1 | 2/2008 | Ali et al. |
| 2008/0287757 A1 | 11/2008 | Berson et al. |

FOREIGN PATENT DOCUMENTS

| | | |
|---|---|---|
| EP | 0793942 | 3/1997 |
| JP | 3939782 | 7/1996 |
| JP | 10337282 A | 12/1998 |
| JP | 2001-245871 | 3/2000 |
| JP | 4038280 | 11/2007 |
| WO | WO 91/11137 | 8/1991 |
| WO | WO 93/06775 | 4/1993 |
| WO | WO 93/13706 | 7/1993 |
| WO | WO 95/16387 | 6/1995 |
| WO | WO 00/61000 | 10/2000 |

* cited by examiner

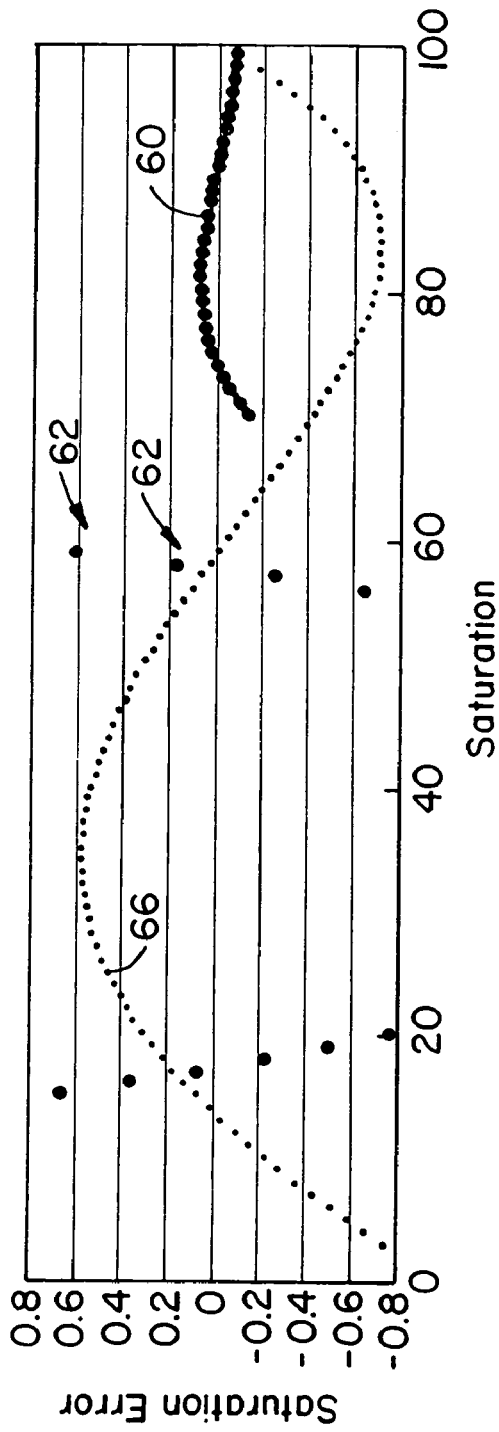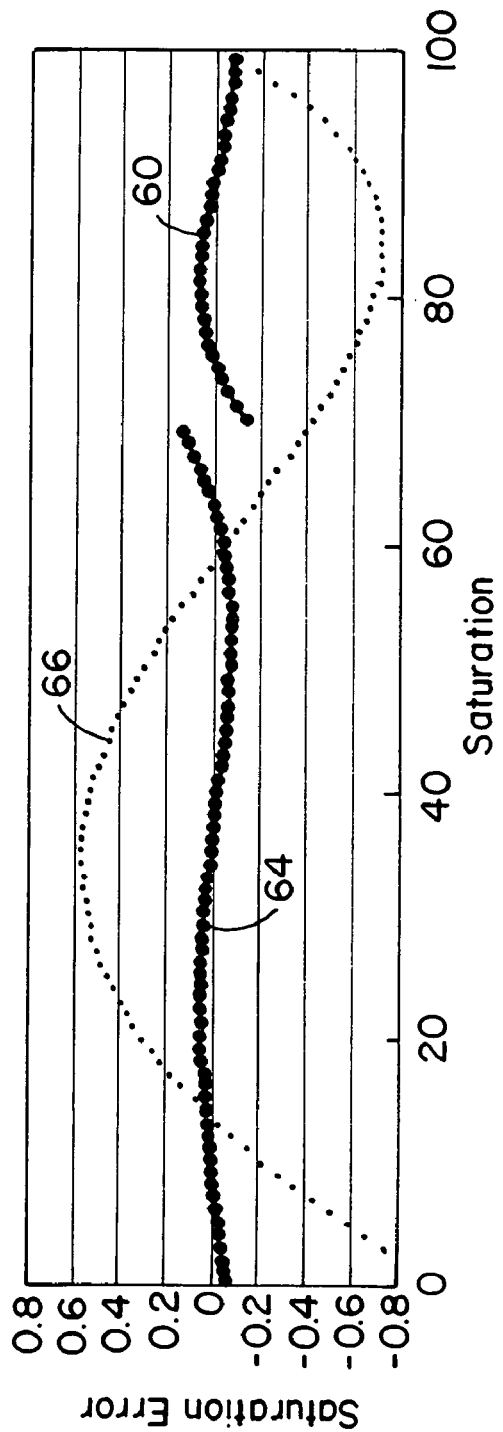
FIG. 5A.
FIG. 5B.

PULSE OXIMETER SENSOR WITH PIECE-WISE FUNCTION

CROSS-REFERENCE TO RELATED APPLICATIONS

This application is a continuation of U.S. application Ser. No. 09/836,050, filed Apr. 16, 2001, now U.S. Pat. No. 6,801,797, which claims the benefit of U.S. Provisional Application No. 60/198,109, filed Apr. 17, 2000, which disclosures are incorporated herein by reference.

BACKGROUND OF THE INVENTION

The present invention relates to oximeter sensors having a memory.

Pulse oximetry is typically used to measure various blood flow characteristics including, but not limited to, the blood-oxygen saturation of hemoglobin in arterial blood, and the rate of blood pulsations corresponding to a heart rate of a patient. Measurement of these characteristics has been accomplished by use of a non-invasive sensor which passes light through a portion of the patient's tissue where blood perfuses the tissue, and photoelectrically senses the absorption of light in such tissue. The amount of light absorbed is then used to calculate the amount of blood constituent being measured.

The light passed through the tissue is selected to be of one or more wavelengths that are absorbed by the blood in an amount representative of the amount of the blood constituent present in the blood. The amount of transmitted or reflected light passed through the tissue will vary in accordance with the changing amount of blood constituent in the tissue and the related light absorption. For measuring blood oxygen level, such sensors have been provided with light sources and photodetectors that are adapted to operate at two different wavelengths, in accordance with known techniques for measuring blood oxygen saturation.

Various methods have been proposed in the past for coding information in sensors, including pulse oximeter sensors, to convey useful information to a monitor. For example, an encoding mechanism is shown in Nellcor U.S. Pat. No. 4,700,708. This mechanism relates to an optical oximeter probe which uses a pair of light emitting diodes (LEDs) to direct light through blood-perfused tissue, with a detector picking up light which has not been absorbed by the tissue. The operation depends upon knowing the wavelength of the LEDs. Since the wavelength of LEDs can vary from device-to-device, a coding resistor is placed in the sensor with the value of the resistor corresponding to the actual wavelength of at least one of the LEDs. When the oximeter instrument is turned on, it first determines the value of the resistor and thus appropriate saturation calculation coefficients for the value of the wavelengths of the LEDs in the probe.

Other coding mechanisms have also been proposed in U.S. Pat. Nos. 5,259,381; 4,942,877; 4,446,715; 3,790,910; 4,303,984; 4,621,643; 5,246,003; 3,720,177; 4,684,245; 5,645,059; 5,058,588; 4,858,615; and 4,942,877, the disclosures of which are all hereby incorporated by reference. The '877 patent in particular discloses storing a variety of data in a pulse oximetry sensor memory, including coefficients for a saturation equation for oximetry.

Nellcor pulse oximeter sensors are encoded with a resistor (RCAL) value that corresponds to the wavelength(s) of the LED(s) within the emitter, such as described in U.S. Pat. No. 4,700,708. Nellcor pulse oximeter instruments read this resistor coding value and use it as a pointer to a look-up table that holds the proper set of coefficients for that sensor for calculating arterial oxygen saturation ($SpO_2$). The function that converts the measured red and IR signal modulation ratio R (also known as the "ratio of ratios" or "rat-rat") to a calculated saturation value is derived from the basic form of the Lambert-Beer Law:

$$R = \frac{\ln(I_1/I_2)_{red}}{\ln(I_1/I_2)_{ir}} = \frac{S \cdot \beta_{O2Hb}^{red} + (1-S) \cdot \beta_{Hb}^{red}}{S \cdot \beta_{O2Hb}^{ir} + (1-S) \cdot \beta_{Hb}^{ir}} = \frac{S \cdot c_1 + (1-S) \cdot c_2}{S \cdot c_3 + (1-S) \cdot c_4} \quad (1)$$

where $I_1$ and $I_2$ refer to detected light signals at two different points in the cardiac cycle, and the β's refer to the characteristic light absorption properties of oxygenated and deoxygenated hemoglobin. When solved for the saturation (S), the result takes on the form:

$$SpO_2 = S \cdot 100 = \frac{c_2 - c_4 \cdot R}{(c_3 - c_4) \cdot R + (c_2 - c_1)} \cdot 100. \quad (2)$$

Equation 2 can be further simplified to require only three constants (by, for example, dividing each constant by $c_2$), but will be used as shown for the remainder of this description. Although theoretically based, the four constants $c_1$-$c_4$ are empirically determined. Theoretical values for the constants are insufficient primarily due to the complexities of light scattering and sensor optics. The values of the sets of constants ($c_1$ through $c_4$) vary with each resistor coding bin (each "bin" corresponding to a range of different characterized LED wavelengths). Multiple sets of coefficients (bins) are provided within a lookup table in Nellcor oximeters. When calculated $SpO_2$ values according to Eq. 2 are less than 70%, a revised value of $SpO_2$ using a linear function is used:

$$SpO_2 = c_5 - c_6 R, \quad (3)$$

where both $c_5$ and $c_6$ vary with the resistor coding value. This linear function was found to better match $SpO_2$ (arterial oxygen saturation as measured by a pulse oximeter) with $SaO_2$ (the true value of arterial oxygen saturation, as measured directly on a blood sample) in observations made at low saturations.

A limitation of this method is that the proper calibration of the pulse oximetry sensor can be accomplished only if the relationship between the signal modulation ratio (R) to blood $SaO_2$ conforms to one of the pre-encoded sets of calibration coefficients.

A further limitation of this method is that the relationship between R and $SaO_2$ of the pulse oximetry sensor may not be linear in a low-saturation region, or that the breakpoint may not optimally be located at 70% $SpO_2$.

A yet further limitation of this prior art method is that the functional relationship between the true arterial oxygen saturation and the measured signals may not fit a single function over the entire span of the measurement range.

SUMMARY OF THE INVENTION

The present invention takes advantage of a memory in the sensor to provide enhanced performance. In one embodiment, not only are the sensor's specific calibration coefficients stored in a memory in the sensor for the formula to determine oxygen saturation, but multiple sets of coefficients are stored. The multiple sets apply to different ranges of saturation values to provide a better fit to occur by breaking the R to SpO2 relationship up into different pieces, each described by a different function. The different functions can also be according to different formulas for determining oxygen saturation.

In another aspect of the invention, the sensor can store a variable breakpoint between the two functions used for oxygen saturation. The two functions could either be separate formulas or the same formula with different coefficients. This allows optimization to a value other than the 70% breakpoint of the prior art.

In another aspect of the present invention, the sensor can store more than one breakpoint to create more than two functions describing the R to SpO2 relationship.

In yet another aspect of the present invention, a spline function is used, breaking up the R to SpO2 relationship into an arbitrary number of regions.

In one embodiment, the coefficients stored in the sensor memory correspond to a non-linear curve for low saturation values below 70% or some other breakpoint(s).

Each of the methods described here improve the fit between the chosen mathematical function and the arterial oxygen saturation by breaking the relationship into subsets of the full measured range and determining optimum coefficients for each range. Spline-fitting, in this context, similarly breaks the full measurement range into subsets to efficiently describe the numerical relational between the underlying tissue parameter of interest and the actual signals being used to estimate its value.

For a further understanding of the nature and advantages of the invention, reference should be made to the following description taken in conjunction with the accompanying drawings.

BRIEF DESCRIPTION OF THE DRAWINGS

FIGS. 5A, 5B, 6A and 6B are graphs illustrating the improved curve fitting of the embodiments of the invention versus the prior art.

DESCRIPTION OF THE SPECIFIC EMBODIMENTS

Sensor Reader/Monitor

Figure 1:
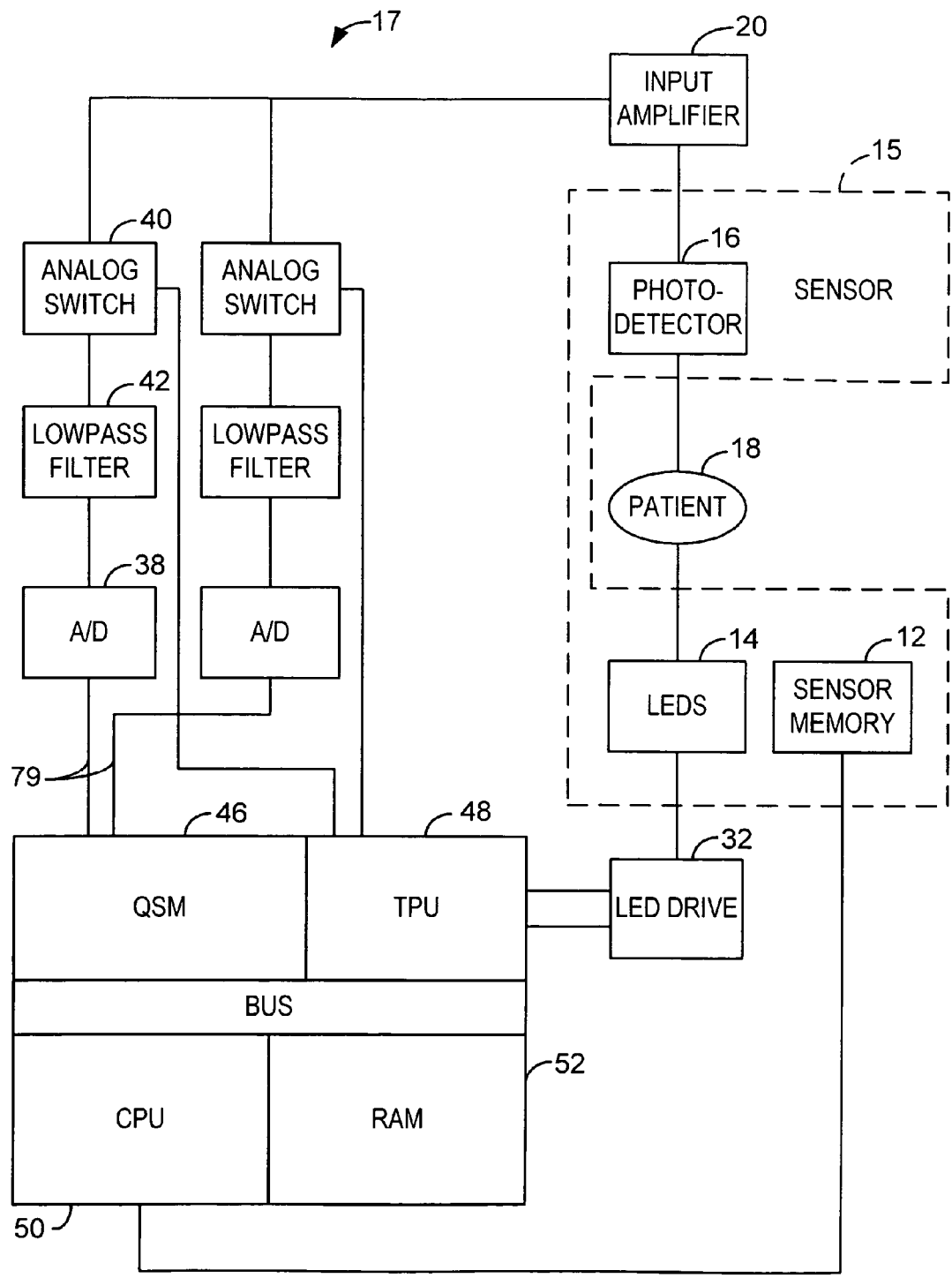
FIG. 1 is a block diagram of a pulse oximeter system incorporating the present invention.

FIG. 1 is a block diagram of one embodiment of the invention. FIG. 1 shows a pulse oximeter 17 (or sensor reader) which is connected to a non-invasive sensor 15 attached to patient tissue 18. Light from sensor LEDs 14 passes into the patient tissue 18, and after being transmitted through or reflected from tissue 18, the light is received by photosensor 16. Either two or more LEDs can be used depending upon the embodiment of the present invention. Photosensor 16 converts the received energy into an electrical signal, which is then fed to input amplifier 20.

Light sources other than LEDs can be used. For example, lasers could be used, or a white light source could be used with appropriate wavelength filters either at the transmitting or receiving ends.

Time Processing Unit (TPU) 48 sends control signals to the LED drive 32, to activate the LEDs, typically in alternation. Again, depending on the embodiment, the drive may control two or any additional desired number of LEDs.

The signal received from input amplifier 20 is passed through two different channels as shown in the embodiment of FIG. 1 for two different wavelengths. Alternately, three channels for three wavelengths could be used, or N channels for N wavelengths. Each channel includes an analog switch 40, a low pass filter 42, and an analog to digital (A/D) converter 38. Control lines from TPU 48 select the appropriate channel at the time the corresponding LED 14 is being driven, in synchronization. A queued serial module (QSM) 46 receives the digital data from each of the channels via data lines 79. CPU 50 transfers the data from QSM 46 into RAM 52 as QSM 46 periodically fills up. In one embodiment, QSM 46, TPU 48, CPU 50 and RAM 52 are part of one integrated circuit, such as a microcontroller.

Sensor Memory

Sensor 15, which includes photodetector 16 and LEDs 14, has a sensor memory 12 associated with it. Memory 12 is connected to CPU 50 in the sensor reader or monitor 17. The memory 12 could be packaged in a body of the sensor 15 or in an electrical plug connected to the sensor. Alternatively, the memory 12 could be packaged in a housing which is attachable to an external surface of the monitor or the memory 12 could be located anywhere in a signal path between the sensor body and the monitor. Specifically, according to some preferred embodiments, a content of the sensor memory 12 could be constant for all sensors associated with a particular sensor model. In this case, instead of putting an individual memory 12 on each sensor associated with this model, the memory 12 could instead be included in a reusable extension cable associated with the sensor model. If the sensor model is a disposable sensor, in this case a single memory 12 would be incorporated into a reusable extension cable. The reusable cable could then be used with multiple disposable sensors.

Figure 2:
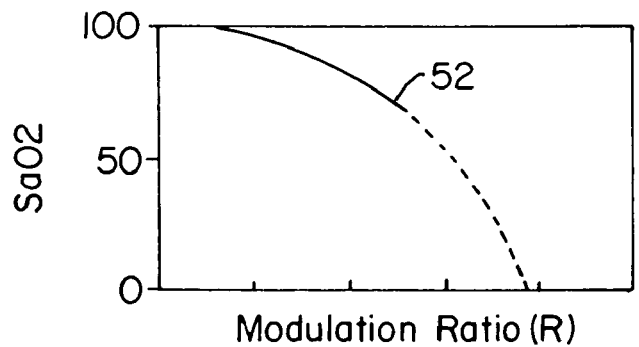
FIG. 2 is a graph of R (signal modulation ratio) versus oxygen saturation ($SaO_2$).

FIG. 2 is an example of a graph of the ratio of ratios (R) on the X axis versus oxygen saturation ($SaO_2$) on the Y axis. Shown is a breakpoint 52. In the prior art, a breakpoint of 70% was pre-defined in the monitor software. To the right of the breakpoint (oxygen saturations between 70-100%) a formula was used with four coefficients. To the left of the breakpoint in the prior art, a linear equation was used with two coefficients. The present invention provides increased flexibility and accuracy by using a non-linear formula for the portion of the curve to the left of breakpoint 52. By using a memory chip in the sensor itself, it is possible to actually store these coefficients on the memory chip, as well as the separate coefficients for the higher saturation values.

In another embodiment of the invention, breakpoint 52 can be stored in the memory chip, and chosen to optimize the curve fitting for the two sets of coefficients. In other words, a better fit to the two curves may be obtained if the breakpoint is 68%, for example. In an alternate embodiment, multiple breakpoints and curves might be used. In addition, rather than using the same formula, different formulas could be used for different sections in another embodiment.

Figure 3:
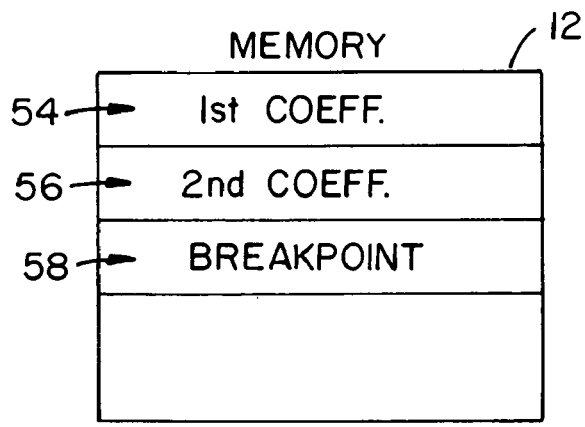
FIG. 3 is a diagram of the contents of a sensor memory according to the invention.

FIG. 3 illustrates the contents of sensor memory 12 of FIG. 1. As illustrated, in a first section of memory 54 are stored a first set of coefficients. A second portion of memory 56 stores a second set of coefficients. Finally, in a third section of memory 58, the breakpoint 52 is stored. Different combinations of these elements could be stored in different memories. For example, the breakpoint could be left out of some, and in others a breakpoint may be provided with only one set of coefficients (with the other set of coefficients in the monitor). Alternately, a breakpoint might be implied from a sensor model number which is stored in the memory, or some other ID value.

β-Equation:

In one embodiment, an enhanced form of the curvilinear function is used. Instead of using Eq.3 (linear) in the lower saturation region, Eq.2 (non-linear) is used for both the upper and lower saturation regions. The breakpoint that defines when to switch coefficients from an upper-region set to a lower-region set is defined by another coefficient. The breakpoint can be programmed either as a value of R, or as a value of $SpO_2$. With the breakpoint defined as a value of R, the algorithm becomes:

$$SpO_2 = \frac{b - d \cdot R}{(c-d) \cdot R + (b-a)} \cdot 100 \quad (4)$$

$$\begin{cases} R \leq c_5: a = c_1, b = c_2, c = c_3, d = c_4 \\ R > c_5: a = c_6, b = c_7, c = c_8, d = c_9 \end{cases}$$

Curve Fitting

Curve fitting to multiple regions follows the same methodology as fitting to a single region. Simply put, the data is partitioned into separate regions and coefficients are determined for each region separately. Commercially available software programs are available, (for example, Mathcad, (Mathsoft, Inc., Cambridge, Mass.). The process can also be found in, for example, Data Reduction and Error Analysis for the Physical Sciences (Philip Beviyton, McGraw-Hill, New York 1969, Ch. 11—Least squares fit to an arbitrary function).

Spline Fitting

An alternate embodiment uses either spline (curve) fitting, or linear or higher order interpolation to a predefined set of $SpO_2$ vs R values ("knots"). A "knot" is a term of art in spline fitting that refers to an x-y pair corresponding to a node on a line, with a number of such knots defining the line. Spline fitting is a technique for interpolation.

For instance, the values of R at specifically defined $SpO_2$ values would be stored in the sensor memory. An example of this looks like:

R=a b c

$SpO_2$=100 95 90

Alternatively, though less preferably, the independent variable could be swapped:

R=0.5 0.6 0.7

$SpO_2$=x y z a) Only the bold values (e.g., a, b and c) would need to be stored with fixed, preselected spaced values of $SpO_2$ (equally spaced or unequally spaced). Or, alternatively, preselected values of R.
b) An alternative approach would store within the sensor memory the $SpO_2$(minimum) and $SpO_2$(maximum) values of the spline range, the number of knots that will be defined, and the sequence of defined values of R for those knots.
c) A further alternative approach could store both $SpO_2$ and the associated R value for each knot.

For each of these options, the instrument would use a spline-fitting algorithm, preferably a cubic spline, to determine the $SpO_2$ at the measured value of R according to the stored values (an alternative could be a linear or higher order interpolation algorithm).

Figure 4:
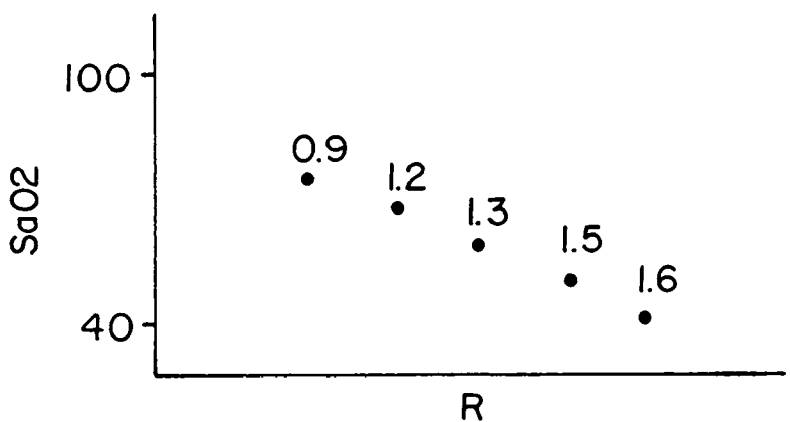
FIG. 4 is a graph of oxygen saturation versus R to illustrate the embodiment for spline or curve fitting to a predefined set of knots.

FIG. 4 illustrates the cubic spline method. FIG. 4 is a graph of oxygen saturation vs. R for a particular sensor emitter. Thus, instead of storing the coefficients as in the prior art method, the actual R or oxygen saturation values are calculated and stored in the sensor memory for that particular sensor's characteristics (e.g., emitter wavelengths). When the oximeter measures the signal level of the light detector, it determines an oxygen saturation value by determining the point on the curve associated with the calculated R value between two of the sample points shown in FIG. 4.

There exists a trade-off in the number of knots defined and the amount of memory required to store them. Too few knots requires very little storage memory, but may not adequately describe the functional relationship; too many over-defines the curve and consumes more memory. The inventors have found that knots spaced 5%-10% apart give adequate results.

Cubic Spline Calculation:

The process for cubic spline interpolation is known to those skilled in the art. Intrinsic in using the spline method is that the value of R needs to be determined first before being translated to $SpO_2$. The preferred process for spline interpolation can be accomplished using the functions provided in Mathcad, and treats the endpoints with cubic functions. Other references for cubic spline interpolations are available.

The process of finding the coordinates of the knots in empirical data with a significant amount of noise may require an additional step. Commercially available basic curve fitting programs may be used (sigmaPlot, or TableCurve, or Mathematical for instance) to determine a best-fit functional approximation to the data. Alternately, one can perform a least-squares fit of an arbitrarily chosen analytical function and pick the values of R at the knot locations ($SaO_2$ values). The analytical function can be an overlapping piece-wise polynomial (e.g., linear or parabolic), or the curvilinear equation of Eq. 1 or Eq. 4. Another approach is to perform a least-squares selection of the knots directly.

FIG. 5A shows the conventional curve fitting of the prior art, wherein a linear relationship is used below 70% saturation, with a curvilinear approach above 70%. The residual error due to an imperfect fit to the actual R to $SaO_2$ response for the curvilinear approach above 70% saturation is illustrated by curve 60, while the residual error of the linear interpolation approach below 70% is illustrated by dots 62. FIG. 5B illustrates the use of curvilinear fits in both regions, with a different curvilinear curve 64 being used below 70%. In this instance, a much improved fit is provided. In both figures, the smaller dotted line 66 corresponds to the use of a single curvilinear fit across both regions, which is also not as accurate, having a much higher error characteristic compared to the curves of the invention, 64 and 60 of FIG. 5B.

Figure 6A:
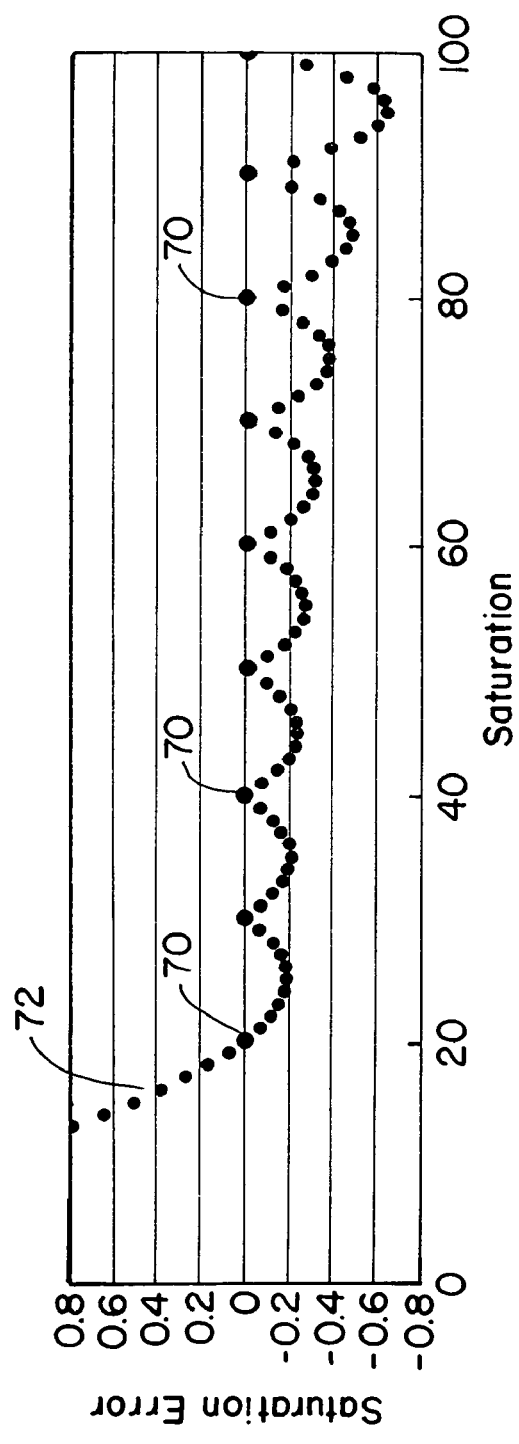
Figure 6B:
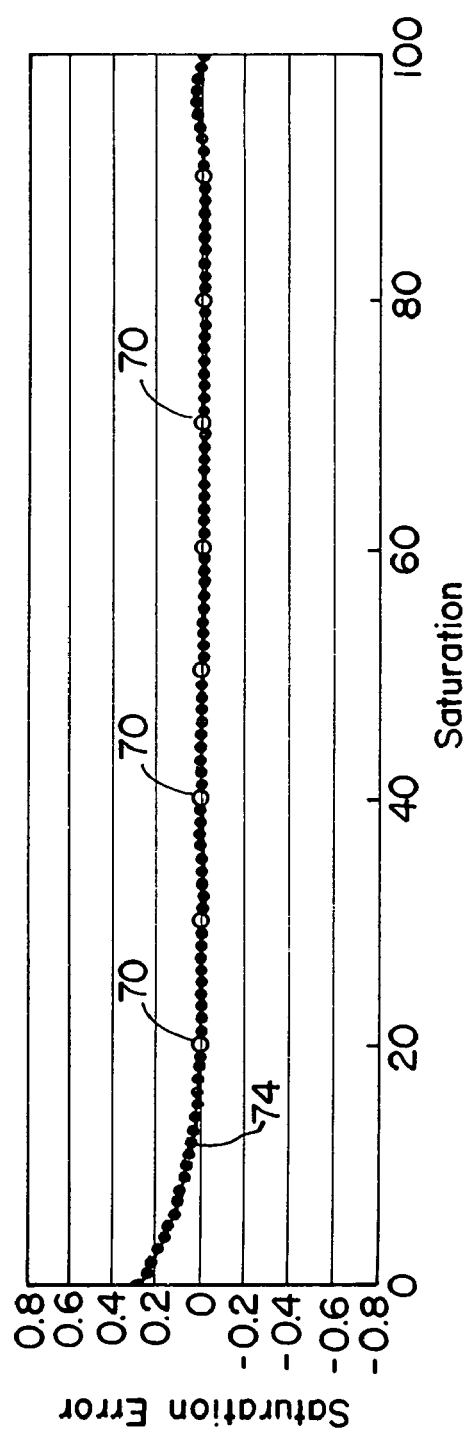

FIGS. 6A and 6B show a plurality of knots as circles 70 on the graphs. Dotted line 72 of FIG. 6A illustrates a linear interpolation fit to these knots, which shows a residual error prone result with multiple loops. In FIG. 6B, on the other hand, the present invention using a cubic spline fitting approach provides a dotted line 74 which is a more accurate fit to the knots 70.

As will be understood by those of skill in the art, the present invention may be embodied in other specific embodiments without departing from the essential characteristics thereof. For example, any function can be used for the formulas for determining oxygen saturation, not just the ones described. For a limited sensor memory, the function representation may be compressed. Any representation of a function could be used. Calibration coefficients may be based on more or different characteristics than the sensor's LED wavelength(s). For example, other LED emitter characteristics or sensor design characteristics can be factors in the sensor's calibration coefficients.

Additionally, the formula for calculating oxygen saturation may be a function of more than the ratio of ratios; for example, other input variables such as signal strength, light levels, and signals from multiple detectors could be used.

This methodology for piece-wise fitting is not limited to oximetry. This method is useful when the relationship between the measured signal and reference value observed during calibration is not adequately described by a single function or set of coefficients over the whole measurement range. The relationship may be broken into subsets, and a piece-wise continuous set of functions may be used to describe the relationship. For example, other blood or tissue constituents could be calculated, such as carboxyhemoglobin, methemoglobin, bilirubin, glucose, lactate, etc. Accordingly, the foregoing description is intended to be illustrative, but not limiting, of the scope of the invention which is set forth in the following claims.

What is claimed is:

1. An oximeter sensor comprising:
a light emitter for directing light at a patient;
a light detector mounted to receive light from the patient; and
a memory storing a first formula for determining oxygen saturation, a second formula for determining oxygen saturation, a first set of coefficients corresponding to a wavelength of the light emitter for use in the first formula, and a second set of coefficients corresponding to the wavelength of the light emitter for use in the second formula, wherein the first formula differs from the second formula.

2. The oximeter sensor of claim 1 wherein the coefficients are dependent on a mean wavelength of the light emitter.

3. The oximeter sensor of claim 1 wherein the memory further stores a value indicating a signal breakpoint between the first and second formulas.

4. The oximeter sensor of claim 3 wherein the value comprises an indication of oxygen saturation.

5. The oximeter sensor of claim 1 wherein at least one of the different formulas is a nonlinear formula.

6. The oximeter sensor of claim 1 wherein the different formulas are linear formulas.

7. The oximeter sensor of claim 1 wherein at least one of the formulas comprises a spline function.

8. The oximeter sensor of claim 1 wherein at least one of the formulas comprises a ratio-of-ratios function.

9. An oximeter sensor system comprising:
a light emitter for directing light at a patient;
a light detector mounted to receive light from the patient; and
a memory, mounted in a sensor or between the sensor and an oximeter monitor, the memory storing an indication of a breakpoint, first and second sets of coefficients corresponding to a same wavelength of the light emitter, and first and second formulas for determining oxygen saturation, the oximeter monitor selecting between the first and second sets of coefficients and the first and second formulas for determining oxygen saturation based at least in part on the breakpoint.

10. The system of claim 9 wherein the coefficients are dependent on a mean wavelength of the light emitter.

11. The system of claim 9 wherein at least one of the formulas is a nonlinear formula.

12. The system of claim 9 wherein the formulas are linear formulas.

13. The system of claim 9 wherein at least one of the formulas comprises a spline function.

14. The system of claim 9 wherein at least one of the formulas comprises a ratio-of-ratios function.

15. The system of claim 9 wherein the breakpoint comprises an oxygen saturation value.

16. An oximeter sensor comprising:
a light emitter for directing light at a patient;
a light detector mounted to receive light from the patient; and
a memory storing at least two different algorithms, and a plurality of alternate values of oxygen saturation or ratio-of-ratio values used in the at least two different algorithms to determine oxygen saturation, the plurality of values corresponding to the same mean wavelength of the same light emitter.

17. The sensor of claim 16 wherein the values correspond to different coefficients or formulas used for different ranges of oxygen saturation.

18. A pulse oximeter system comprising:
a pulse oximeter sensor comprising:
a light emitter for directing light at a patient;
a light detector mounted to receive light from the patient; and
a memory storing a first formula for determining oxygen saturation, a second formula for determining oxygen saturation, a first set of coefficients corresponding to a wavelength of the light emitter for use in the first formula, and a second set of coefficients corresponding to the wavelength of the light emitter for use in the second formula, wherein the first formula differs from the second formula; and
a pulse oximeter monitor configured to receive communications from the pulse oximeter sensor and configured to perform calculations using one or both of the first and second formulas to estimate oxygen saturation in blood of the patient.

19. The system of claim 18 wherein the coefficients are dependent on a mean wavelength of the light emitter.

20. The system of claim 18 wherein the memory further stores a value indicating a signal breakpoint between the first and second formulas.

21. The system of claim 20 wherein the value comprises an oxygen saturation level.

22. The system of claim 18 wherein at least one of the different formulas is a nonlinear formula.

23. The system of claim 18 wherein the different formulas are linear formulas.

24. The system of claim 18 wherein at least one of the formulas comprises a spline function.

25. The system of claim 18 wherein at least one of the formulas comprises a ratio-of-ratios function.

26. An oximeter system comprising:
an oximeter sensor, comprising:
a light emitter configured to direct light at a patient;
a light detector mounted to receive light from the patient; and
a sensor memory storing a first formula for determining oxygen saturation, a second formula for determining oxygen saturation, a first set of coefficients corresponding to a wavelength of the light emitter, and a second set of coefficients corresponding to the wavelength of the light emitter;

an oximeter monitor, comprising:

a calculation mechanism configured to determine a blood oxygen saturation in the patient, wherein the calculation mechanism selects and utilizes the first set of coefficients in the first formula for a first range of oxygen saturation values and selects and utilizes the second set of coefficients in the second formula for a second range of oxygen saturation values, wherein the first range differs from the second range.

27. The system of claim 26 wherein the coefficients are dependent on a mean wavelength of the light emitter.

28. The system of claim 26 wherein at least one of the different formulas is a nonlinear formula.

29. The system of claim 26 wherein the different formulas are linear formulas.

30. The system of claim 26 wherein at least one of the different formulas comprises a spline function.

31. The system of claim 26 wherein at least one of the different formulas comprises a ratio-of-ratios function.

32. The system of claim 26 wherein the sensor memory further stores a value indicating a signal breakpoint between the first and second formulas.

33. The system of claim 32 wherein the value comprises an oxygen saturation level.

* * * * *